US008853170B2

(12) United States Patent
Bagley et al.

(10) Patent No.: US 8,853,170 B2

(45) Date of Patent: Oct. 7, 2014

(54) COMPOSITIONS COMPRISING SUGAR-CYSTEINE PRODUCTS

(75) Inventors: David Bagley, Kaysville, UT (US); Scott Momii, Rancho Palos Verdes, CA (US); Scott Nagasawa, Rancho Palos Verdes, CA (US); Herbert T. Nagasawa, Irvine, CA (US)

(73) Assignee: Max International, LLC, Midvale, UT (US)

(*) Notice: Subject to any disclaimer, the term of this patent is extended or adjusted under 35 U.S.C. 154(b) by 348 days.

(21) Appl. No.: 13/015,952

(22) Filed: Jan. 28, 2011

(65) Prior Publication Data

US 2011/0183927 A1 Jul. 28, 2011

Related U.S. Application Data

(60) Provisional application No. 61/299,046, filed on Jan. 28, 2010, provisional application No. 61/357,053, filed on Jun. 21, 2010.

(51) Int. Cl.

| | |
|---|---|
| ***A61K 31/7056*** | (2006.01) |
| ***A61P 3/02*** | (2006.01) |
| ***A61P 9/10*** | (2006.01) |
| ***A23L 1/30*** | (2006.01) |
| ***A23L 2/52*** | (2006.01) |
| ***A61K 31/198*** | (2006.01) |
| ***A61K 31/7004*** | (2006.01) |
| ***A23L 1/305*** | (2006.01) |
| ***A23L 2/60*** | (2006.01) |
| ***A61K 31/7008*** | (2006.01) |
| ***A61K 9/00*** | (2006.01) |
| ***A23L 1/302*** | (2006.01) |
| ***A61K 31/426*** | (2006.01) |
| ***A23L 1/304*** | (2006.01) |

(52) U.S. Cl.

CPC ............. *A61K 31/426* (2013.01); *A23L 1/3002* (2013.01); *A23L 2/52* (2013.01); *A61K 31/198* (2013.01); *A61K 31/7004* (2013.01); *A23L 1/3051* (2013.01); *A23L 2/60* (2013.01); *A61K 31/7008* (2013.01); *A61K 9/0095* (2013.01); *A23L 1/30* (2013.01); *A23L 1/302* (2013.01); *A23L 1/304* (2013.01)

USPC ........................................................... 514/23

(58) Field of Classification Search

USPC ........................................................... 514/23

See application file for complete search history.

(56) References Cited

U.S. PATENT DOCUMENTS

| | | | | |
|---|---|---|---|---|
| 4,320,145 | A * | 3/1982 | Cavazza | 514/23 |
| 4,335,210 | A | 6/1982 | Meister et al. | |
| 4,605,644 | A | 8/1986 | Foker | |
| 4,647,571 | A * | 3/1987 | Meister et al. | 514/369 |
| 4,719,201 | A | 1/1988 | Foker | |
| 4,736,060 | A | 4/1988 | Tomuro et al. | |
| 4,868,114 | A | 9/1989 | Nagasawa et al. | |
| 5,292,538 | A | 3/1994 | Paul et al. | |
| 5,631,234 | A | 5/1997 | Ozawa et al. | |
| 6,218,366 | B1 | 4/2001 | Cyr et al. | |
| 6,534,480 | B2 | 3/2003 | Cyr et al. | |
| 6,572,899 | B1 | 6/2003 | Gorsek | |
| 6,730,336 | B2 | 5/2004 | Villagran et al. | |
| 6,964,969 | B2 * | 11/2005 | McCleary | 514/283 |
| 7,153,503 | B1 * | 12/2006 | Henderson | 424/638 |
| 7,455,857 | B2 * | 11/2008 | Henderson et al. | 424/464 |
| 2003/0108624 | A1 | 6/2003 | Kosbab | |
| 2004/0219235 | A1 | 11/2004 | Pushpangadan | |
| 2006/0105972 | A1 * | 5/2006 | Nagasawa | 514/43 |
| 2006/0280854 | A1 | 12/2006 | De Roos et al. | |
| 2007/0116838 | A1 | 5/2007 | Prakash et al. | |
| 2007/0160590 | A1 * | 7/2007 | McCleary | 424/94.1 |
| 2007/0190209 | A1 | 8/2007 | Sinnott | |
| 2007/0243270 | A1 * | 10/2007 | Evans et al. | 424/729 |
| 2009/0042822 | A1 | 2/2009 | Nagasawa | |
| 2009/0042850 | A1 | 2/2009 | Basnakian et al. | |
| 2010/0074969 | A1 | 3/2010 | Hughes et al. | |
| 2011/0183927 | A1 | 7/2011 | Bagley et al. | |
| 2011/0184185 | A1 | 7/2011 | Nagasawa et al. | |
| 2011/0287109 | A1 | 11/2011 | Bagley et al. | |

FOREIGN PATENT DOCUMENTS

| | | | |
|---|---|---|---|
| EP | 0257992 | A2 | 3/1988 |
| JP | 6145054 | | 5/1994 |
| JP | 10139665 | | 5/1998 |
| WO | 9218120 | | 10/1992 |
| WO | 2006055597 | A1 | 5/2006 |

OTHER PUBLICATIONS

Bognar et al, Liebigs Ann. Chem. 1970, 738, 68-78.*

Jarrows Formulas, BroccoMax, Feb. 21, 2009, Jarrow Formulas, webpage found via Wayback Machine.

Chen et al., "Modification of Surface Charges of Soy Protein by Phospholipids," (1985) 62:1686-1689.

Office Action dated Jul. 3, 2010 received in related U.S. Appl. No. 13/113,585.

Qanungo et al., "N-Acetyl-L-cysteine enhances apoptosis through inhibition of nuclear factor-kappaB in hypoxic murine embryonic fibroblasts," Journal of Biochemical Chemistry (2004) 279(48):50455-50464.

Roberts, J. C., et al., Differential chemoprotection against acetaminophen-induced hepatotoxicity by latentiated L-cysteines, Chem Res Toxicol. Nov. 1998;11(11):1274-82.

Roberts, J. C., et al., Protection against acetaminophen hepatotoxicity by ribose-cysteine (RibCys), Pharmacol Toxicol. Apr. 1992;70(4):281-5.

(Continued)

*Primary Examiner* — Ganapathy Krishnan

(74) *Attorney, Agent, or Firm* — Pepper Hamilton LLP

(57) ABSTRACT

The present invention provides compositions comprising sugar, cysteine, and/or sugar-cysteine products.

5 Claims, No Drawings

(56) References Cited

OTHER PUBLICATIONS

Roberts, J. C., et al., L-cysteine prodrug protects against cyclophosphamide urotoxicity without compromising therapeutic activity, Cancer Chemother Pharmacol. 1991;28(3):166-70.

Non-Final Office Action for co-pending U.S. Appl. No. 10/990,933 dated Aug. 21, 2007.

Final Office Action for co-pending U.S. Appl. No. 10/990,933 dated Jan. 31, 2008.

Non-Final Office Action for co-pending U.S. Appl. No. 12/182,354 dated Mar. 29, 2010.

Final Office Action for co-pending U.S. Appl. No. 12/182,354 dated Oct. 15, 2010.

Advisory Action for co-pending U.S. Appl. No. 12/182,354 dated Jan. 10, 2011.

Radomski et al., Thiazolidine-4(R)-carboxylic acids derived from sugars: Part I, C-2-epimerisation in aqueous solutions, Carbohydrate Research (1989) 187(2):223-237.

Non-Final Office Action dated Jan. 23, 2013 received in co-pending U.S. Appl. No. 13/015,941.

Non-Final Office Action dated Jul. 3, 2012 received in co-pending U.S. Appl. No. 13/113,585.

Final Office Action dated Dec. 11, 2012 received in co-pending U.S. Appl. No. 3/113,585.

Lenarczyk, M., et al., The "pro-drug" RibCys decreases the mutagenicity of high-LET radiation in cultured mammalian cells, Radiat Res. Nov. 2003;160(5):579-83.

Roberts, J. C., et al., Prodrugs of L-cysteine as protective agents against acetaminophen-induced hepatotoxicity. 2-(Polyhydroxyalkyl)- and 2-(polyacetoxyalkyl)thiazolidine-4(R)-carboxylic acids, J Med Chem. Oct. 1987;30 (10):1891-6.

Roberts, J. C., et al., Time course for the elevation of glutathione in numerous organs of L1210-bearing CDF1 mice given the L-cysteine prodrug, RibCys, icol Lett. Dec. 1991;59(1-3):245-51.

Roberts, J. C., et al., Chemoprotection against cyclophosphamide-induced urotoxicity: ribose-cysteine, Anticancer Res. Mar.-Apr. 1994;14(2A):383-7.

Rowe, J. K., et al., Protective effect of RibCys following high-dose irradiation of the rectosigmoid, Dis Colon Rectum. Jul. 1993;36(7):681-8.

Bognar, R., et al., Substituierte Thiazolidine durch Reaktion von L-Cystein mit Monosacchariden, Liebigs Ann. Chem., 1970;738:68-78.

Roberts, J. C., et al., Thiazolidine Prodrugs of Cysteamine and Cysteine as Radioprotective Agents, Radiation Research, 1995;143:203-213.

Roberts, J.C. and Francetic, D.J., Mechanisms of Chemoprotection by D-Ribose-L-Cysteine, A Thiazolidine Prodrug of L-Cysteine, Med. Chem. Res., 1991a;1:213-219.

Lucas Slitt, A.M., et al., Effect of Ribose Cysteine Pretreatment on Hepatic and renal Acetaminophen Metabolite Formation and Glutathione Depletion, Basic Clin. Pharmaco. Toxicol., 2005:96:487-494.

Lucas, A.M., et al, Ribose Cysteine Protects Against Acetaminophen-Induced Hepatic and Renal Toxicity, Toxicol Pathol. Sep.-Oct. 2000;28(5):697-704.

Weitzel, J., et al., [Demonstration and formation tendency of sugar-cysteine compounds and their complex salts. Stability constants of zinc and cobalt (II) complexes], Hoppe Seylers Z Physiol Chem. Aug. 6, 1959;315:236-55.

Arfsten, D.P., et al, Impact of 30-day oral dosing with N-acetyl-L-Cysteine 5 on Sprague-Dawley rat physiology, Int J Toxicol. Jul.-Aug. 2004;23(4):239-47.

Baker, D.H., Comparative species utilization and toxicity of sulfur amino acids, J Nutr. Jun. 2006;136(6 Suppl):1670S-1675S.

Ball, R.O., et al, The in vivo sparing of methionine by Cysteine in sulfur amino acid requirements in animal models and adult humans, J Nutr. Jun. 2006;136(6 Suppl):1682S-1693S.

Brosnan, J. and Brosnan, M., The Sulfur-Containing Amino Acids: An Overview, J Nutr. Jun. 2006;136(6 Suppl):1636S-1640S.

Cerny, C. and Davidek, T., Formation of Aroma Compounds from Ribose and Cysteine during the Maillard Reaction, J Agric Food Chem. Apr. 23, 2003;51(9):2714-21.

Cooper, A.J.L., et al., On the Chemistry and Biochemistry of 3-Mercaptopyruvic Acid, the α-Keto Acid Analog of Cysteine, J Biol Chem. Jan. 25, 1982;257(2):816-26.

Fukagawa, N., Sparing of Methionine requirements: Evaluation of Human Data Takes Sulfur Amino Acids beyond Protein, J Nutr. Jun. 2006;136(6 Suppl):1676S-1681S.

Garlick, P.J., The nature of human hazards associated with excessive intake of amino acids, J Nutr. Jun. 2004;134 (6 Suppl):1633S-1639S; discussion 1664S-1666S, 1667S-1672S.

Griffiths, J.C., et al., Sub-chronic (13-week) oral toxicity study with D-Ribose in Wistar rats, Food Chem Toxicol. Jan. 2007;45(1):144-52.

Griffiths, J.C., et al., Lack of oral embryotoxicity/teratogenicity with D-Ribose in Wistar rats, Food Chem Toxicol. Mar. 2007;45(3):388-95.

Gross, C.L., et al., Biochemical manipulation of intracellular glutathione levels influences cytotoxicity to isolated human lymphocytes by sulfur mustard, Cell Biol Toxicol. Jul.-Sep. 1993;9(3):259-67. doi:10.1007/BF00755604. PMID 8299004.

Gross, M. and Zollner, N., Serum levels of glucose, insulin, and C-peptide during long term D-Ribose administration in man, Klin Wochenschr. Jan. 4, 1991;69(1):31-6.

Gross, M., et al., Metabolism of D-ribose administered continuously to healthy persons and to patients with myoadenylate deaminanse deficiency, Klin Wochenschr. Dec. 4, 1989;67(23):1205-13.

Harper, A.E., et al, Effects of Ingestion of Disproportionate Amounts of Amino Acids, Physiological Reviews, 1970;60(8): 428-558 (see pp. 449 5-452).

Joseph, C.K., Nutritional Supplements: Amino acids and their derivatives, American Journal of Pharmaceutical Education, 2003;66:157-164.

Kitahori, Y.,et al, Lack of carcinogenicity of L-Cysteine monohydrochloride in fischer 344 rats, J. Toxicol. Pathol., 1997;10:83-89.

Klavins, J.V., Effects of administration of excessive amounts of sulphur containing amino acids: L-cystine, Brit. J. Exptl. Pathol., 1963;44:516-519.

Kleinveld, H.A., et al, Failure of N-acetylCysteine to reduce low-density lipoprotein oxidizability in healthy subjects, Eur J. Clin. Pharmacol., 1992;43: 26 639-642.

Kwyer, Thomas, MD: The Role of Glutathione in Cell Defenses with references to Clinical Deficiencies and Treatment. http://www.fda.gov/ohrms/dockets/ac/00/slides/3652s1_05/sld001.htm.

Nagasawa, H.T., et al., Epimerization at C-2 of 2-substituted 5 thiazolidine-4-carboxylic acids, J. Heterocyclic Chem., 1981;18:1047-1051.

Olney, J. W., et al., Cytotoxic effects of acidic and sulphur containing amino acids on the infant mouse central nervous system, Exp. Brain. Res., 1971;14:61-76.

Pompella, A., et al., The changing faces of glutathione, a cellular protagonist, Biochem Pharmacol., Oct. 15, 2003;66(8):1499-503.. doi:10.1016/S0006-2952(03)00504-5. PMID 14555227. http://linkinghub.elsevier.com/retrieve/pii/S0006295203005045.

Sauberlich, H. E., Studies on the toxicity and antagonism of amino acids for weanling rats, J. Nutr., 1961;75:61-72.

Sawamoto, O., et al., Four-Week Intravenous Repeated Dose Toxicity Study of L-Cysteine in Male Rats, J. Toxicol. Sci., 2003;28(2):95-107.

Stipanuk, M.H., et al., Mammalian Cysteine metabolism: new insights into regulation of Cysteine metabolism, J. Nutr., 2006;136:1652S-16595S.

Sumioka, I., et al, Acetaminophen-Induced Hepatotoxicity: Still an Important Issue, Yonago Acta Medica, 2004;47: 17-28.

Tribble, D.L., et al, HyperCysteinemia and delayed sulfur excretion in cirrhotics after oral Cysteine loads, Am. J. Clin. Nutr., 1989;50:1401-22 1406.

(56) References Cited

OTHER PUBLICATIONS

Van Boekel, M.A.J.S., Formation of flavour compounds in the Maillard reaction, Biotechnology Advances, 2006 24:230-233.
Van De Poll, M., et al, Adequate Range for Sulfur-Containing amino Acids and Biomarkers for Their Excess: Lessons from Enteral and Parenteral Nutrition, J. 29 Nutr., 2006;136:1694S-1700S.
Vina, J., et al, The effect of Cysteine oxidation on isolated hepatocytes, Biochem. J., 1983;212:39-44.
Jaeschke, H., Glutathione Disulfide as Index of Oxidant Stress in Rat Liver During Hypoxia, Am. J. Physiol. Gastrointes. Liver Physiol., 1990:258, Abstract Only, Retrieved from the Internet, <URL:http://www.ncbi.nlm.nih.gov/sites/entrez>.
Klassen, C. D., et al., Role of sulfhydryls in the hepatotoxicity of organic and metallic compounds, Fundamental and Applied Toxicology, 1985;5:806-15.
Carroll, M. P., et al., Efficacy of radiportective agents in preventing small and large bowel radiation injury, Dis Colon Rectum., Jul. 1995;38(7):716-22.
Nagasawa, H. T., et al., 2-Substituted thiazolidine-4(R)-carboxylic acids as prodrugs of L-cysteine, Protection of mice against acetaminophen hepatotoxicity, J. Med. Chem., 1984;27(5):591-96.
Roberts, J. C., et al., Thiazolidine prodrugs of cysteamine and cysteine as radioprotective agents, Radiat Res. Aug. 1995;143(2):203-13.
Roberts, J. C., et al., Biodistribution of [35S]-Cysteine and cysteine prodrugs: potential impact on chemoprotection strategies, Journal of Labelled Compounds and Radiopharmaceuticals, 1999;42:485-95.
Wilmore, B. H., et al., Thiazolidine prodrugs as protective agents against gamma-radiation-induced toxicity and mutagenesis in V79 cells, J Med Chem. Aug. 2, 2001;44(16):2661-6.
Oz, H. S., et al., Comparative efficacies of 2 cysteine prodrugs and a glutathione delivery agent in a colitis model, Transl Res. Aug. 2007;150(2):122-9.
Bantseev, V., et al., Antioxidants and cataract: (cataract induction in space environment and application to terrestrial aging cataract), Biochem Mol Biol Int. Sep. 1997;42(6):1189-97.
Notice of Allowance dated Apr. 8, 2013 received in copending U.S. Appl. No. 12/182,354.

* cited by examiner

COMPOSITIONS COMPRISING SUGAR-CYSTEINE PRODUCTS

CROSS-REFERENCE TO RELATED APPLICATIONS

This application claims priority to U.S. Provisional Application No. 61/299,046, filed Jan. 28, 2010, and U.S. Provisional Application No. 61/357,053, filed Jun. 21, 2010, each of which is hereby incorporated by reference in its entirety.

FIELD OF THE INVENTION

The present invention is directed, in part, to compositions comprising sugar-cysteine products, methods of preparing the same, and to methods of using the same.

BACKGROUND OF THE INVENTION

Cysteine prodrugs are useful for protecting animals against radiation-related deaths, effects caused by radiation poisoning, and acetaminophen-induced hepatotoxicity (Lenarczyk et al., Radiation Res., 2003, 160, 579-583; Roberts et al., J. Med. Chem., 1987, 30, 1891). Cysteine prodrugs, such as, 2(R,S)-D-ribo-(1',2',3',4'-tetrahydroxybutyl)thiazolidine-4 (R)-carboxylic acid (RibCys), have been used in methods to enhance delivery of glutathione and ATP levels in cells (see, U.S. Patent Publication No. 2009-0042822). Although there have been uses described for other cysteine prodrugs, such as N-acetylcysteine (NAC), compositions to deliver cysteine to an animal have been limited due to, for example, instability and/or the reactivity of the exposed sulfhydryl (SH) group of cysteine. Thus, there is a long-felt need to solve the problem of how to deliver cysteine to an animal in a convenient form. The present invention solves this need as well as others.

SUMMARY OF THE INVENTION

In some embodiments, the present invention provides compositions comprising a sugar and cysteine, wherein the ratio of the sugar to cysteine is greater than 1.0:1.0 (mol/mol).

In some embodiments, the present invention provides compositions comprising a sugar-cysteine product. In some embodiments, the sugar-cysteine product is RibCys, GlcCys, GlycCys, FruCys, $GlcNH_2Cys$, or GlcNHAcCys, or any combination thereof.

In some embodiments, the present invention provides compositions suitable for animal consumption.

In some embodiments, the present invention provides beverages and/or foodstuffs comprising a composition described herein.

In some embodiments, the present invention provides compositions comprising a sugar-cysteine product, a sugar, and free-cysteine, wherein the composition comprises less than 1% w/v or less than 1% w/w of free-cysteine. In some embodiments, the sugar and the sugar of the sugar-cysteine product are the same sugar. In some embodiments, the sugar-cysteine product is RibCys, GlcCys, GlycCys, FruCys, $GlcNH_2Cys$, or GlcNHAcCys.

In some embodiments, the compositions are substantially free of free-cysteine.

In some embodiments, the present invention provides a beverage or food container comprising a composition or a mixture of compositions described herein.

In some embodiments, the present invention provides methods of preparing an aqueous solution of a sugar-cysteine product comprising contacting the aqueous solution with a sugar and cysteine, wherein the ratio of the sugar to cysteine is greater than 1.0:1.0 (e.g. w:w or mol:mol).

In some embodiments, the present invention provides methods of delivering a sugar-cysteine product to an animal comprising administering a composition described herein to the animal. In some embodiments, the composition is prepared by a method described herein.

DESCRIPTION OF EMBODIMENTS

The present invention provides compositions comprising one or more sugars and cysteine, methods of making the same, and methods of using the same. The present invention also provides compositions comprising one or more sugar-cysteine products and methods of making the same. The present invention also provides foodstuffs and beverages comprising one or more sugars, cysteine, sugar-cysteine products, or combinations thereof, and methods of making the same.

Throughout the present specification, various sugars, amino acids, and other molecules that have both D and L forms are disclosed. Unless explicitly stated otherwise, recitation of the sugar, amino acid, or other molecule can refer to the D-form, L-form, or a mixture of both. In some embodiments, the sugar, amino acid, or molecule will be free of the D-form, i.e. 100% L-form. Likewise, in some embodiments, the sugar, amino acid, or molecule will be free of the L-form, i.e., 100% of D-form. For example, the term "ribose" can refer to D-ribose, L-ribose, or a mixture of both. Additionally, the term "cysteine" refers to L-cysteine, D-cysteine, or a mixture of both. These are non-limiting examples and other molecules referred to herein can also have D- and L-forms, which are also included within the presently described inventions.

As used herein, the singular forms "a," "an," and "the" include plural references unless the context clearly dictates otherwise.

As used herein, the term "about" means±5% of the value being modified. Thus, "about 1" means from 0.95 to 1.05." As used herein, the term "about" as it is used in a range or a series modifies each member of the range or the series. For example, in the phrases "about 1-5" or "about 1 to 5" the term "about" modifies both the 1 and the 5 as well as the numbers in between 1 and 5. Also, for example, "about 1, 2, 3, 4, or 5" the term "about" modifies each of 1, 2, 3, 4, or 5. Additionally, a range or series that is modified by the term "about" also discloses the same range (including the endpoints) or series not modified by the term "about." For example, the phrase "about 1-5" also discloses the range (including the endpoints) "1-5." Additionally, the phrase a range of "X-Y" is equivalent to "X to Y" and includes the endpoints "X" and "Y." For example "1-5" is equivalent to "1 to 5."

As used herein, the phrase "sugar-cysteine product" refers to a product that forms when a sugar and cysteine react with one another. Examples of sugar-cysteine products include, but are not limited to, ribose-cysteine (RibCys), glucose-cysteine (GlcCys), fructose-cysteine (FruCys), glyceraldehyde-cysteine (GlycCys), glucosamine-cysteine ($GlcNH_2Cys$), and N-acetylglucosamine-cysteine (GlcNHAcCys), and/or any combination thereof.

As used herein, the term "sugar" refers to a saccharide. The saccharide can be either a polysaccharide or a monosaccharide. In some embodiments, the monosaccharide is an aldose monosaccharide. Monosaccharides include, but are not limited to, fructose, glucose, ribose, and the like. In some embodiments, the sugar is mannose, arabinose, xylose, rhamnose, lyxose, galactose, or the like. The sugar can also be an amino sugar. Examples of amino sugars include, but are not limited to, N-acetylglucosamine, galactosamine, glucosamine, and the like. In some embodiments, the compositions and methods described herein are free of glucose or are at least free of detectable glucose. In some embodiments, the compositions and methods described herein are free of fructose or are at least free of detectable fructose. The compositions can also be free of sucrose or are at least free of detectable sucrose. In some embodiments, the compositions and methods described herein are free of all sugars or are at least free of any detectable sugars, except for the sugar forming the sugar-cysteine product.

In some embodiments, the compositions described herein comprise about 1-1000 mg of a sugar. In some embodiments, the composition comprises about 1-900, 1-800, 1-700, 1-600, 1-500, 1-400, 1-300, 1-200, 1-100, 1-50, or 1-25 mg of a sugar. In some embodiments, the composition comprises about 100-300, 200-300, or 225-275 mg of a sugar. In some embodiments, the compositions comprises about 50, 100, 150, 200, 250, 300, 400, 500, 600, 700, 800, 900, or 1000 mg of a sugar. In some embodiments, the compositions comprises at least 50, 100, 150, 200, 250, 300, 400, 500, 600, 700, 800, 900, or 1000 mg of a sugar. In some embodiments, the composition comprises about 0.1-0.5, about 0.2-0.5, about 0.3-0.4, about 0.3-0.5% w/w of the sugar.

As used herein, the term "ratio" refers to the amounts of two or more compounds, molecules, and the like, compared to one another. The ratio can be, for example, in terms of absolute weight (e.g., grams to grams; wt:wt). The ratio can be also be, for example, determined by comparing concentrations of each compound (e.g., molarity to molarity; mol:mol). The ratio can also be in terms of moles of each molecule present in the composition. For example, a composition comprising a first and second compound each with 10 mmol would be said to be in a 1 to 1 ratio (i.e., 1.0:1.0).

As used herein, the term "substantially" means at least 95%, at least 96%, at least 97%, at least 98%, or at least 99%.

As used herein, the term "RibCys" refers to 2(R,S)-D-ribo-(1',2',3',4'-tetrahydroxybutyl)thiazolidine-4(R)-carboxylic acid. The chemical name can also be referred to as "(4R)-2-(1,2,3,4-tetrahydroxybutyl)thiazolidine-4-carboxylic acid." RibCys is the sugar-cysteine product of ribose and cysteine. RibCys can be represented by formula I:

I

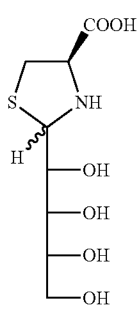

As used herein, the term "GlcCys" is a sugar-cysteine product that refers to the product of glucose and cysteine. "GlcCys" can be represented by formula II:

II

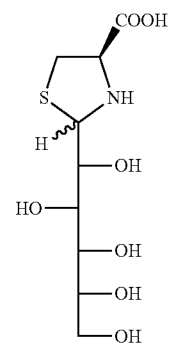

As used herein, the terms and phrases "foodstuff," "food supplement," "beverage," and "beverage supplement" have the normal meanings for those terms, and are not restricted to pharmaceutical or nutraceutical preparations. Other composition forms are also included within the present invention. These may, for example, include pure or substantially pure compound such as a foodstuff precursor (such as a rehydratable powder), or a beverage precursor (such as a powder dispersible in water, milk, or other liquid). In some embodiments the foodstuff, foodstuff supplement, beverage, or beverage supplement is frozen. In some embodiments, the foodstuff, foodstuff supplement, beverage, or beverage supplement is not frozen. The beverage can also be in the form of a slurry where the beverage is a mix of liquid and solid. A beverage or foodstuff is something that is suitable for animal consumption. In some embodiments, the beverage or foodstuff is suitable for human consumption. A composition is suitable for animal or human consumption is something that can be ingested without causing harm to the animal or human. Other examples of animals include, but are not limited to, a human, a cat, a dog, a pig, a cow, a horse, a sheep, and the like.

In addition to the compositions described herein, the present invention also provides solid form preparations which are intended to be converted, shortly before use, to liquid form preparations for oral administration to an animal (e.g., oral administration). Such liquid form preparations include solutions, suspensions, and emulsions. These particular solid form preparations can be provided in a unit dose form. The unit dose form can provide convenience to the user. The unit dose form can be used to provide a single liquid dosage unit. Alternately, sufficient solid form preparations may be provided so that after conversion to liquid form, multiple individual liquid doses may be obtained by measuring predetermined volumes of the liquid form preparation as with a syringe, teaspoon, or other volumetric container or apparatus. In some embodiments, when multiple liquid doses are so prepared, the unused portion of the liquid doses can be kept at low temperature (i.e., under refrigeration) to, for example, maintain stability.

The compositions described herein can also comprise one or more of flavoring agent(s), flavor modifier(s), flavor enhancer(s), colorant(s), stabilizer(s), buffer(s), artificial and/or natural sweetener(s), dispersant(s), thickener(s), solubilizing agent(s), and the like. Liquids utilized for preparing the liquid form preparation may be for example, water, fruit juice, vegetable juice, milk, alcohol, and the like, or any mixture thereof.

As used herein, a "flavor" refers to the perception of taste and/or smell in an animal, which include sweet, sour, salty, bitter, umami, and others. The animal may be a human.

As used herein, a "flavoring agent" refers to a compound, or a biologically acceptable salt thereof, that induces a flavor or taste in an animal or a human.

As used herein, a "flavor modifier" refers to a compound, or biologically acceptable salt thereof, that modulates, including enhancing or potentiating, and inducing, a taste and/or smell of a natural or synthetic flavoring agent in an animal or a human.

As used herein, a "flavor enhancer" refers to a compound, or biologically acceptable salt thereof, that enhances a taste or smell of a natural or synthetic flavoring agent. In some embodiments, the flavoring agent is a "savory flavor," which refers to the savory "umami" taste typically induced by MSG (mono sodium glutamate) in an animal or a human.

Other examples of flavoring agents include, but are not limited to, "sweet flavoring agent," "sweet compound," or "sweet receptor activating compound," which herein refer to a compound, or biologically acceptable salt thereof, that elicits a detectable sweet flavor in an animal, e.g., sucrose, fructose, glucose, and other known natural saccharide-based sweeteners, or known artificial sweeteners including, but not limited to, sucralose, saccharine, cyclamate, and aspartame. A sweet flavoring agent can also be referred to as a sweetener.

Other examples of sweeteners include, but are not limited to, sucrose, high fructose corn syrup, invert sugar(s), crystalline fructose, fructose polymer(s), aspartame, glucose, glucose polymer(s), sucralose, saccharine, and mixtures thereof. In some embodiments, the sweetener can be, but is not limited to, sucrose, crystalline fructose, fructose polymer(s), glucose, glucose polymer(s), aspartame, sucralose, acesulfame K, fructose syrup, glucose syrup, corn syrup, invert sugar, sugar alcohol(s), maple syrup, honey, fruit syrup(s) (e.g., apple, grape, and/or pear) and/or mixtures thereof. In some embodiments, the composition can be non-dietetic or dietetic. In some embodiments, the sweetener agent for a non-dietetic composition is crystalline fructose, fructose syrup, corn syrup and/or fruit syrups. In some embodiments, the sweetener agent for a dietetic composition is sucralose, aspartame, acesulfame K and/or any mixture thereof.

In some embodiments, where crystalline fructose is used as a sweetening agent, from about 0.01 g to about 50.0 g can be used per 354 ml of beverage solution. If a fructose polymer is used as a sweetening agent, from about 0.1 g to about 1000 g can be used per 354 ml of beverage solution.

If sucrose is used as a sweetener, from about 0.01 g to about 100 g can be used per 354 ml of beverage solution. If aspartame is used as a sweetener, from about 0.05 g to about 30 g can be used per 354 ml of beverage solution. If sucralose is used as a sweetener, from about 0.01 g to about 30 g can be used per 354 ml of beverage solution. If acesulfame K is used as a sweetener, from about 0.01 g to about 20 g can be used per 354 ml of beverage solution. If a glucose polymer is used as a sweetener, from about 0.01 g to about 1000 g can be used per 354 ml of beverage solution. If glucose is used as a sweetener, from about 0.01 g to about 100 g can be used per 354 ml of beverage solution.

If saccharine is used as a sweetener, from about 0.01 g to about 10 g can used per 354 ml of beverage solution. If fructose syrup is used as a sweetener, from about 0.5 g to about 100 g can be used per 354 ml beverage solution. If glucose syrup is used as a sweetener, from about 0.3 ml to about 100 ml can be used per 354 ml beverage solution. If corn syrup is used as a sweetener, from about 0.5 ml to about 100 ml can be used per 354 ml beverage solution. If an invert sugar is used as a sweetener, from about 0.5 g to about 100 g can be used per 354 ml beverage solution. If a sugar alcohol is used as a sweetener, from about 0.2 g to about 100 g can be used per 354 ml beverage solution. If maple syrup is used as a sweetener, from about 0.1 g to about 100 g can be used per 354 ml beverage solution. If honey is used as a sweetener, from about 1.0 g to about 100 g can be used per 354 ml beverage solution. If a fruit syrup (e.g., apple, grape, and/or pear) is used as a sweetener, from about 1.0 g to about 100 g can be used per 354 ml beverage solution. If crystalline fructose, a fructose polymer, fructose syrup, glucose, glucose syrup, corn syrup, invert sugar, sugar alcohol, maple syrup, honey, fruit syrup (apple, grape, pear), acesulfame K, glucose polymer, sucrose, aspartame, saccharine, sucralose and/or any mixture thereof is used as a sweetener, from about 0.01 g to about 200 g can be used per 354 ml of beverage solution.

In some embodiments, the composition (e.g., foodstuff or beverage) can also comprise a flavoring agent such as, for example, chocolate fudge, chocolate, vanilla, strawberry, prairie berry, mocha, latte, peach, almond, coconut, raspberry, saskatoon berry, plains berry, apple, orange, butterscotch, coffee, blueberry, bubble gum, cola, root beer, guarana and/or any mixture thereof. In some embodiments, flavoring agents and/or any mixture thereof chosen from the list above can be added from about 0.01 g to about 50 g per 354 ml of a beverage solution.

In some embodiments, the composition comprises a preservative. The preservative used can be natural and bacteriostatic. In some embodiments, the preservative is benzoic acid and/or a benzoate compound such as, but not limited to, sodium benzoate, potassium lactate, calcium benzoate and/or magnesium benzoate. In some embodiments, the beverage compositions comprise from about 0.15 g to about 0.70 g of preservative, such as benzoic acid, sodium benzoate, potassium benzoate, calcium benzoate, magnesium benzoate and/or any mixture thereof per 354 ml of beverage solution.

The beverage composition can also comprise the addition of carbonation, i.e., the forceful introduction of carbon dioxide gas, under pressure, against a liquid surface, which causes the absorption of the gas into, and in the case of the present compositions, solubilization by the liquid. In some embodiments, from about 0.10 volume to about 4 volumes of gas is added per 354 ml of beverage solution. The higher the gas pressure and the cooler the liquid, the more carbonation that is dissolved. Carbonation can, for example, enhance the flavor, sweetness, taste, mouth-feel and/or lowering the pH of the beverage. Carbonation can also change the viscosity to render the beverage more desirable.

In addition to sugar, cysteine, and the sugar-cysteine product, the compositions described herein can comprise other ingredients. Examples of additional ingredients include, but are not limited to, vitamin(s), mineral(s), amino acid(s), antioxidant(s), botanical extract(s), and the like. Particular examples include, but are not limited to, vitamin C, vitamin E, glutamine, L-carnitine, N-acetyl cysteine (NAC), alpha lipoic acid, Co Enzyme Q 10, Cordyceps, N-Acetyl glucosamine, quercetin, lutein (zeaxanthin), milk thistle extract (e.g., *silybum marianum*), silimarin, theanine, curcumin (turmeric), broccoli sprouts (sulforaphane), green tea, and the like. In some embodiments, the composition can comprise one or more of the following: Vitamin B1 (thiamine), Vitamin B2 (Riboflavin), Vitamin B3 (Niacin), Vitamin B6 (Pyridoxine HCl), Vitamin B12 (Cyanocobalamin), folic acid, pantothenic acid, biotin, chromium nicotinate, magnesium carbonate, copper gluconate, ginseng (e.g. *panax ginseng*), rhodiola rosea, acetyal-L-carnitine, caffeine (e.g. naturally derived or synthetic), and the like. The composition can also be caffeine free. In some embodiments, the composition can comprise at least 10 of the foregoing. In some embodiments, the composition can comprise all of the foregoing.

As used herein, the phrase "recommended daily allowance" or "recommended dietary allowance" refers to an amount to be consumed by an individual that has generally been determined to be desirable. In some embodiments, the individual is a male, female, infant (0-12 months), child (1-10 years), pregnant woman, lactating woman (first 6 months post-partum or 6-12 months post-partum). The male or female can be 11-18 years old or greater than or equal to 19 years old. The recommended daily allowance can be found, for example, in *Recommended Dietary Allowances: 10th Edition*, Subcommittee on the Tenth Edition of the RDAs, Food and Nutrition Board, Commission on Life Sciences, National Research Council, NATIONAL ACADEMY PRESS, Washington, D.C. 1989, which is hereby incorporated by reference in its entirety. The daily allowances referred to herein and below are determined for a male greater than or equal to 19 years old, but can routinely be converted to other types of subjects as needed.

In some embodiments, vitamin B3 is kosher. In some embodiments, vitamin B6 is kosher. In some embodiments, vitamin B12 is kosher. In some embodiments, the composition as a whole is kosher or could be certified kosher. In some embodiments, any of the ingredients can be kosher.

In some embodiments, the present invention provides compositions comprising a sugar and cysteine. In some embodiments, the ratio of the sugar to the cysteine is 1.0:1.0. In some embodiments, the ratio of the sugar to the cysteine is greater than 1.0:1.0. For example, the ratio of sugar to cysteine can be about 1.1:1.0, about 1.5:1.0, about 2.0:1.0, about 2.5:1.0, about 3.0:1.0, about 4.0:1.0, about 5.0:1.0, about 6.0:1.0, about 7.0:1.0, about 8.0:1.0, about 9.0:1.0, about 10.0:1.0, or the like. In some embodiments the ratio of the sugar to cysteine is from about 2.0:1.0 to about 10.0:1.0. In some embodiments, the ratio of the sugar to cysteine is greater than about 2.0:1.0, greater than about 3.0:1.0, greater than about 4.0:1.0, greater than about 5.0:1.0, greater than about 6.0:1.0, greater than about 7.0:1.0, greater than about 8.0:1.0, greater than about 9.0:1.0, or greater than about 10.0:1. In some embodiments the ratio of the sugar to cysteine is from about 2.0:1.0 to about 5.0:1.0.

In some embodiments, the cysteine is L-cysteine. In some embodiments, the cysteine is a cysteine salt. For example, the cysteine salt can be, but is not limited to, the cysteine hydrochloride salt. In some embodiments, the cysteine is a salt monohydrate. In some embodiments, the composition is free of a cysteine salt. In some embodiments, the composition is free of a cysteine salt monohydrate.

As used herein, the phrase "substantially free of free-cysteine" refers to a composition where free-cysteine cannot be detected using standard HPLC methods or similar standard methods. In some embodiments, the composition comprises less than 1 ppm of free-cysteine.

In some embodiments, the composition further comprises a bicarbonate. The bicarbonate can be used to counteract the acidity of the cysteine salt when it is dissolved in a liquid. Examples of bicarbonates include, but are not limited to, potassium bicarbonate, sodium bicarbonate, and the like. The carbonate can also be used, for example, to cause a fizzing in the liquid.

When mixed under permissive conditions, ribose and cysteine will combine to form RibCys. Accordingly, in some embodiments, a composition can comprise ribose, cysteine, and RibCys. In some embodiments, a composition comprises ribose and RibCys and is free of free-cysteine. In some embodiments, a composition comprises ribose and RibCys and is substantially free of free-cysteine. "Free-cysteine" refers to a cysteine molecule that has a free sulfhydryl group that would be able to react with other molecules and be involved in oxidation reactions. RibCys does not contain free-cysteine because the sulfhydryl group is not available to be used in an oxidation reaction. RibCys can be hydrolyzed non-enzymatically to produce free-cysteine and free-ribose, but this would not mean that RibCys comprises free-cysteine. RibCys can be present in an equilibrium with free-ribose and free-cysteine if there is not excess ribose as compared to the cysteine. Accordingly, the composition can comprise excess ribose such that RibCys is maintained as the sugar-cysteine product and not be allowed to dissociate into free-ribose and free-cysteine. In some embodiments, the ratio of the sugar (e.g. ribose) to sugar-cysteine product (e.g. ribose-cysteine) in the composition is about 1.1:1 to 3:1, about 1.1:1 to 5:1, about 1.1:1 to 10:1, 1.5:1 to 3:1, about 1.5:1 to 5:1, about 1.5:1 to 10:1, about 2:1 to 3:1, about 2:1 to 5:1, about 2:1 to 10:1, about 2.5:1, about 2.5:1 to 3:1, about 2.5:1 to 5:1, about 2.5 to 10:1, greater than or equal to 2:1, greater than or equal to 1.5:1, greater than or equal to 2.5:1. The ratio of the sugar to the sugar-cysteine product can be determined based upon w/w. The compositions can also be free of any of the ingredients or components listed herein. That is, the present specification provides, in some embodiments, compositions that comprise one or more of the listed ingredients or components as described herein, but in some embodiments, the composition is free of one or more of the listed ingredients herein.

In some embodiments, a composition comprises about 100-300% of the recommended daily allowance of vitamin B1. In some embodiments, a composition comprises about 100, 200, or 300% of the daily allowance of vitamin B1. In some embodiments, a composition comprises less than or equal to 300% of the daily allowance of vitamin B1. In some embodiments, a composition comprises less than 250% of the daily allowance of vitamin B1. In some embodiments, a composition comprises about 1-5 mg vitamin B1 (thiamine). In some embodiments, a composition comprises about 1, 2, 3, 4, or 5 mg of Vitamin B1. In some embodiments, a composition comprises 3 mg of Vitamin B1. In some embodiments, a composition comprises about 0.004-0.005% w/w of Vitamin B1. In some embodiments, the Vitamin B1 is thiamine HCl.

In some embodiments, a composition comprises about 100-300% of the recommended daily allowance of vitamin B2. In some embodiments, a composition comprises about 100, 200, or 300% of the daily allowance of vitamin B2. In some embodiments, a composition comprises less than or equal to 300% of the daily allowance of vitamin B2. In some embodiments, a composition comprises less than 200% of the daily allowance of vitamin B2. In some embodiments, a composition comprises about 1-5, about 1-4, about 1-3, about 1-2, about 1.5 to 2.0 mg vitamin B2 (riboflavin). In some embodiments, a composition comprises about 1, 2, 3, 4, or 5 mg of Vitamin B2. In some embodiments, a composition comprises less than 2 mg of Vitamin B2. In some embodiments, a composition comprises about 0.002-0.003%, about 0.002-0.004%, about 0.002-0.005% w/w of Vitamin B2. In some embodiments, the Vitamin B2 is riboflavin.

In some embodiments, a composition comprises about 100-300% of the recommended daily allowance of vitamin B3 (niacin). In some embodiments, a composition comprises about 100, 200, or 300% of the daily allowance of vitamin B3. In some embodiments, a composition comprises less than or equal to 300% of the daily allowance of vitamin B3. In some embodiments, a composition comprises less than 200% of the daily allowance of vitamin B3. In some embodiments, a composition comprises about 1-50, about 1-40, about 1-30, about 1-20, about 10-30, about 10-25, about 10-40, about 10-50, about 15 to 25 mg vitamin B3 (niacin). In some embodiments, a composition comprises about 10, 20, 30, 40, or 50 mg of Vitamin B3. In some embodiments, a composition comprises less than 25 mg of Vitamin B3. In some embodiments, a composition comprises about 0.02-0.05%, about 0.02-0.04%, about 0.02-0.035%, about 0.03-0.04%, or about 0.03-0.035% w/w of Vitamin B3. In some embodiments, the Vitamin B3 is niacin.

In some embodiments, a composition comprises about 100-500% of the recommended daily allowance of vitamin B6 (pyridoxine HCl). In some embodiments, a composition comprises about 100, 150, 200, 250, 300, 350, 400, 450, or 500% of the daily allowance of vitamin B6. In some embodiments, a composition comprises less than or equal to 300% of the daily allowance of vitamin B6. In some embodiments, a composition comprises less than or equal to 250% of the daily allowance of vitamin B6. In some embodiments, a composition comprises about 1-10, about 1-6, about 1-5, about 1-4, about 1-3, about 1-2, about 1-10, about 4 to 6, about 5, about 1, about 2, about 3, about 4, about 5, about 6, about 7, about 8, about 9, about 10 mg vitamin B6. In some embodiments, a composition comprises less than 10 mg of Vitamin B6. In some embodiments, a composition comprises about 0.005-0.010%, 0.005-0.009%, 0.005-0.008%, 0.006-0.008%, or about 0.007-0.008%, w/w of Vitamin B6. In some embodiments, the Vitamin B6 is pyridoxine HCl.

In some embodiments, a composition comprises about 100-2000% of the recommended daily allowance of vitamin B12 (cyanocobalamin). In some embodiments, a composition comprises about 100, 150, 200, 250, 300, 350, 400, 450, 500, 550, 600, 650, 700, 750, 800, 850, 900, 1000, 1100, 1200, 1300, 1400, 1500, 1600, 1700, 1000-2000, 1200-1800, 1300-1700, 1600-1700, 1650-1700, at least 1500, at least 1600, at least 1650 percent of the daily allowance of vitamin B12. In some embodiments, a composition comprises about 1-100, 1-75, 1-60, about 1-50, about 1-40, about 1-30, about 40-60, about 45-55, or about 50, mcg vitamin B12. In some embodiments, a composition comprises about $1.00\times10^{-5}$ to $8.00\times10^{-5}$%, about $2.00\times10^{-5}$ to $8.00\times10^{-5}$%, about $3.00\times10^{-5}$ to $8.00\times10^{-5}$%, about $4.00\times10^{-5}$ to $8.00\times10^{-5}$%, about $6.00\times10^{-5}$ to $8.00\times10^{-5}$%, or about $7.00\times10^{-5}$ to $8.00\times10^{-5}$% w/w of Vitamin B12. In some embodiments, the Vitamin B12 is cyanocobalamin 1%.

In some embodiments, a composition comprises about 100-500% of the recommended daily allowance of folic acid. In some embodiments, a composition comprises about 100, 150, 200, 250, 300, 350, 400, 450, or 500% of the daily allowance of folic acid. In some embodiments, a composition comprises less than or equal to 300% of the daily allowance of folic acid. In some embodiments, a composition comprises less than or equal to 200% of the daily allowance of folic acid. In some embodiments, a composition comprises about 100-1000, about 100-900, about 100-800, about 100-700, about 100-600, about 100-500, about 100-400, about 300-500, about 350-450, about 375-425 mcg of folic acid. In some embodiments, a composition comprises about 0.0001-0.0007%, about 0.0002-0.0007%, about 0.0003-0.0007%, about 0.0004-0.0007%, about 0.0005-0.0007%, about 0.0006-0.0007% w/w of folic acid.

In some embodiments, a composition comprises about 100-300% of the recommended daily allowance of panthothenic acid. In some embodiments, a composition comprises about 100, 200, or 300% of the daily allowance of panthothenic acid. In some embodiments, a composition comprises less than or equal to 300% of the daily allowance of panthothenic acid. In some embodiments, a composition comprises less than 200% of the daily allowance of panthothenic acid. In some embodiments, a composition comprises about 1-50, about 1-40, about 1-30, about 1-20, about 1-10, about 10-30, about 10-25, about 10-40, about 10-50, about 5 to 15 mg, about 7.5 to 12.5 mg panthothenic acid. In some embodiments, a composition comprises about 5, 10, 20, 30, 40, or 50 mg of panthothenic acid. In some embodiments, a composition comprises less than 15 mg of panthothenic acid. In some embodiments, a composition comprises about 0.010-0.016%, about 0.011-0.016%, about 0.012-0.016%, about 0.013-0.016%, about 0.014-0.016%, or about 0.015-0.016% w/w of panthothenic acid.

In some embodiments, a composition comprises about 25-500% of the recommended daily allowance of biotin. In some embodiments, a composition comprises about 25, 50, 75, 100, 150, 200, 250, 300, 350, 400, 450, or 500% of the daily allowance of biotin. In some embodiments, a composition comprises less than or equal to 100% of the daily allowance of biotin. In some embodiments, a composition comprises less than or equal to 50% of the daily allowance of biotin. In some embodiments, a composition comprises about 50, about 100, about 125, about 150, about 175, about 200, about 250, about 300, about 25-300, about 25-200, about 25-175, about 25-150, about 50-200, about 50-150, about 75-175, about 75-150, about 100-200, about 100-175, about 100-150, about 125-175, about 125-150, or about 135-165, mcg of biotin. In some embodiments, a composition comprises about 0.0001-0.0003%, 0.0002-0.0003%, about 0.0001-0.0004%, or about 0.0002-0.0004% w/w of biotin.

In some embodiments, a composition comprises about 1-50% of the recommended daily allowance of chromium. In some embodiments, a composition comprises about 1, 5, 10, 15, 20, 25, 30, 35, 40, 45, or 50% of the daily allowance of chromium. In some embodiments, a composition comprises about 1-50, about 1-40, about 1-30, about 5-50, about 5-40, about 5-30, about 10-50, about 10-40, about 10-30, about 20-50, about 20-40, about 20-30, about 25-50, about 25-40, about 25-35, about 10, about 20, about 30, about 40, or about 50 mcg of chromium. In some embodiments, a composition comprises about $1\times10^{-5}$-$5\times10^{-5}$%, about $2\times10^{-5}$-$5\times10^{-5}$%, about $3\times10^{-5}$-$5\times10^{-5}$%, or about $4\times10^{-5}$-$5\times10^{-5}$%, w/w of chromium. The chromium can be supplied in any form, such as, but not limited to, chromium nicotinate. In some embodiments, the chromium nicotinate is chromium nicotinate 0.5%.

In some embodiments, a composition comprises about 1-100% of the recommended daily allowance of magnesium. The magnesium can be supplied in various form such as, but not limited to, magnesium carbonate. In some embodiments, the magnesium carbonate is magnesium carbonate 27%. In some embodiments, a composition comprises about 1, 5, 10, 15, 20, 25, 30, 40, 50, 60, 70, 80, 90, 100% of the daily allowance of magnesium. In some embodiments, a composition comprises about 1-10, 1-5, 5, or at least 5% of the daily allowance of magnesium. In some embodiments, a composition comprises about 1-50, about 1-40, about 1-30, about 1-20, about 10-20, about 15-20, about 10-40, about 10-50, about 15 to 25 mg of magnesium. In some embodiments, a composition comprises about 10, 20, 30, 40, or 50 mg of magnesium. In some embodiments, a composition comprises at least 20 mg of magnesium. In some embodiments, a composition comprises about 0.02-0.05%, about 0.02-0.04%, about 0.02-0.035%, about 0.03-0.04%, or about 0.03-0.035% w/w of magnesium (e.g. magnesium carbonate).

In some embodiments, a composition comprises about 1-100% of the recommended daily allowance of copper. The copper can be supplied in any form such as, but not limited to, copper gluconate. In some embodiments, a composition comprises about 1, 2, 3, 4, 5, 6, 7, 8, 9, 10, 15, 20, 25, 30, 40, 50, 60, 70, 80, 90, 100% of the daily allowance of copper. In some embodiments, a composition comprises about 1-10, 1-9, 1-8, or at least 8% of the daily allowance of copper. In some embodiments, a composition comprises about 0.01-2, about 0.01-1, about 0.01-0.5, about 0.01-0.4, about 0.01-0.3, about 0.01-0.2, about 0.1-0.2, about 0.15-0.2, about 0.2 mg of copper. In some embodiments, a composition comprises 0.1, 0.2, 0.3, 0.4, or 0.5 mg of copper. In some embodiments, a composition comprises at least 0.2 mg of copper. In some embodiments, a composition comprises about 0.0001-0.0004, about 0.0002-0.0004, or about 0.0003-0.0004% w/w of copper.

In some embodiments, the composition comprises quercetin. In some embodiments, the composition comprises about 1-400, about 1-300, about 1-200, about 1-100, about 1-75, about 25-75, about 45-55, about 40-60, about 47-52, about 50 mg of quercetin. In some embodiments, the composition comprises 10, 20, 30, 40, 50, 60, 70, 80, 90, or 100 mg of quercetin. In some embodiments, the composition comprises at least 10, 20, 30, 40, 50, 60, 70, 80, 90, or 100 mg of quercetin. In some embodiments, a composition comprises about 0.01-0.08, about 0.02-0.08, about 0.03-0.08, about 0.04-0.08, about 0.05-0.08, about 0.06-0.08, or about 0.07-0.08% w/w of quercetin.

In some embodiments, the composition comprises CoQ10, which can also be referred to as Coenzyme Q10, ubiquinone, ubidecarenone, or coenzyme Q. In some embodiments, the composition comprises about 1-100, about 1-75, about 1-50, about 1-25, about 1-20, about 10-30, about 15-25, about 17-22, about 20 mg of CoQ10. In some embodiments, the composition comprises 10, 20, 30, 40, 50, 60, 70, 80, 90, or 100 mg of CoQ10. In some embodiments, the composition comprises at least 10, 20, 30, 40, 50, 60, 70, 80, 90, or 100 mg of CoQ10. In some embodiments, a composition comprises about 0.01-0.05, about 0.02-0.05, about 0.03-0.05, about 0.04-0.05, about 0.03-0.04, about 0.03-0.035, or about 0.03-0.05% w/w of CoQ10.

In some embodiments, the composition comprises about 1-1000 mg of ginseng. The ginseng can be from any source such as, but not limited to, *Panax quinquefolius* or *Panax ginseng*. Therefore, the term ginseng encompasses, but is not limited to *Panax quinquefolius* or *Panax ginseng*. In some embodiments, the ginseng is *Panax ginseng*. In some embodiments, the ginseng is *Panax quinquefolius*. In some embodiments, the ginseng is free of *Panax quinquefolius*. In some embodiments, the ginseng is free of *Panax ginseng*. In some embodiments, the composition comprises about 1-900, 1-800, 1-700, 1-600, 1-500, 1-400, 1-300, 1-200, 1-100 mg ginseng. In some embodiments, the composition comprises at least 25, 50, 75, 100, 150, or 200 mg ginseng. In some embodiments, the composition comprises about 0.05-0.20, 0.10-0.20, 0.15-0.20, 0.15-0.16, 0.15-0.17, 0.15-0.18, or 0.15-0.19% w/w of ginseng.

In some embodiments, the composition comprises rhodiola rosea, which can also be referred to as Golden Root, Roseroot, or Aaron's Rod. In some embodiments, the composition comprises about 1-400, about 1-300, about 1-200, about 1-100, about 1-75, about 25-75, about 45-55, about 40-60, about 47-52, about 50 mg of rhodiola rosea. In some embodiments, the composition comprises 10, 20, 30, 40, 50, 60, 70, 80, 90, or 100 mg of rhodiola rosea. In some embodiments, the composition comprises at least 10, 20, 30, 40, 50, 60, 70, 80, 90, or 100 mg of rhodiola rosea. In some embodiments, a composition comprises about 0.01-0.08, about 0.02-0.08, about 0.03-0.08, about 0.04-0.08, about 0.05-0.08, about 0.06-0.08, or about 0.07-0.08% w/w of rhodiola rosea.

In some embodiments, the composition comprises acetyl-L-carnitine. In some embodiments, the composition comprises about 1-1000, 1-900, 1-800, 1-700, 1-600, 1-500, 1-400, 1-300, 1-200, 1-100, 1-50, 100-500, 100-400, 100-300, 100-200, 200-300, 225-275 mg of acetyl-L-carnitine. In some embodiments, the composition comprises about 0.1-0.5, about 0.2-0.5, about 0.3-0.4, about 0.3-0.5% w/w of acetyl-L-carnitine.

In some embodiments, the composition comprises caffeine. In some embodiments, the composition is caffeine free. In some embodiments, the caffeine is supplied by a natural product, e.g. green tea. In some embodiments, the composition comprises 1-100 mg of caffeine. In some embodiments, the composition comprises 1-75, 1-50, 1-40, 1-35, 30-40, or 30-50 mg of caffeine. In some embodiments, the composition comprises 30-35 mg of caffeine. In some embodiments, the composition comprises 32 mg of caffeine. In some embodiments, the composition comprises caffeine derived from green tea. In some embodiments, to yield "X" mg of caffeine in the final product "2X" mg of the natural product (e.g. green tea) is used. In some embodiments, the composition comprises about 0.04-0.06% or about 0.05-0.06% w/w of caffeine.

In some embodiments, the composition also comprises water, fructose, natural flavors, citric acid, stevia extract, guar gum, xanthum gum, sodium benzoate, potassium sorbate, or a combination thereof. In some embodiments, the guar gum and the xanthum gum are pre-combined.

In some embodiments, the composition comprises about 1000-5000, 2000-4000, 2500-3500 mg of fructose. In some embodiments, the composition comprises about 1000, 2000, 3000, 4000, or 5000 mg of fructose. In some embodiments, the composition comprises at least 1000, 2000, 3000, 4000, or 5000 mg of fructose. In some embodiments, the composition comprises about 1-10%, about 1-9%, about 4-6%, about 4-5%, or about 4.5-5.0% w/w of fructose.

The natural flavors can be any natural flavors. In some embodiments, the composition comprises about 100-200 mg of natural flavors. In some embodiments, the composition comprises about 0.2 to 0.3% w/w of natural flavors.

In some embodiments, the composition comprises citric acid. In some embodiments, the composition comprises about 100-200 mg of citric acid. In some embodiments, the composition comprises about 0.2-0.3% w/w of citric acid.

In some embodiments, the composition comprises stevia extract. In some embodiments, the composition comprises about 1-100, 1-90, 1-80, 1-70, 1-60, 1-50, 1-40, 1-30, 1-20, 20-40, 30-40, or 35-40 mg of stevia extract. In some embodiments, the composition comprises about 0.06-0.07% w/w of stevia extract.

In some embodiments, the composition comprises a blend of guar gum and xanthum gum. In some embodiments, the composition comprises 50-100, 70-100, 75-100, or 70-80 mg of a blend of guar gum and xanthum gum. In some embodiments, the blend of guar gum and xanthum gum represents about 0.10-0.20% w/w of the composition. The blend of guar gum and xanthum gum can be any where from 1% guar gum to 99% xanthum gum or 1% xanthum gum to 99% guar gum.

In some embodiments, the composition comprises sodium benzoate and/or potassium sorbate. In some embodiments, the composition comprises about 1-100, 10-50, 10, 20, 30, 40, 50 of sodium benzoate and/or potassium sorbate or some other preservative. In some embodiments, the composition comprises at least 10, 20, 30, 40, 50 of sodium benzoate and/or potassium sorbate or another preservative. In some embodiments, the composition comprises 0.04-0.05% w/w of sodium benzoate and/or potassium sorbate or some other preservative. In some embodiments, when the composition comprises both sodium benzoate and potassium sorbate, the composition can comprise anywhere from 1% sodium benzoate and 99% potassium sorbate to 1% potassium sorbate and 99% sodium benzoate.

As discussed herein, additional ingredients can be added to the composition and the remaining weight can be filled by water. For example, in some embodiments, the composition comprises about 90-99, 90-98, 90-97, 90-96, 90-95, 90-94, or 93-94% w/w of water. In some embodiments, the composition comprises at least 90, 91, 92, 93, 94, 95, 96, 97, 98, 99, or 99.9% w/w of water.

In some embodiments, a composition comprises one or more of, at least 10 of, or all of the following: vitamin B1, vitamin B2, vitamin B3, vitamin B6, vitamin B12, folic acid, panthothenic acid, biotin, chromium nicotinate, magnesium carbonate, copper gluconate, quercetin, CoQ10, *panax ginseng*, rhodiola rosea, ribose, ribose-cysteine, acetyl-L-carnitine, water, and optionally caffeine, The compositions described herein can be made according to any mixing protocol. In some embodiments, the raw materials are prepared as a blend and then dissolved in water simultaneously. In some embodiments, the solution is filtered to remove any non-dissolved material. In some embodiments, each ingredient is added sequentially to the water. In some embodiments, the aqueous composition is heat pasteurized. In some embodiments, the composition is aliquoted into dosage forms, such as, but not limited to 2 liquid ounce forms to 4 liquid ounce forms. In some embodiments, the composition is not heat pasteurized and a bottle or package is cold-filled with the aqueous composition.

In some embodiments, the composition is gluten free. In some embodiments, the composition is free of artificial or synthetic preservatives.

In some embodiments, the amount of free-cysteine present in a composition is less than 10%, less than 9%, less than 8%, less than 7%, less than 6%, less than 5%, less than 4%, less than 3%, less than 2%, less than 1%, less than 0.5%, less than 0.25%, or less than or 0.1%. The percent of free-cysteine in a composition can be determined by w/w or w/v. In some embodiments, the amount of free-cysteine is less than 1 ppm.

As discussed herein, the compositions described herein can be in the form of a powder. This powder can be a powdered beverage mix that can be added to a liquid to make a beverage. Accordingly, the compositions described herein can also be a beverage. In some embodiments, the beverage is a 2 ounce beverage, a 4 ounce beverage, or a beverage from 2 ounces to 4 ounces. The powder can also be mixed with other powdered beverage mixes. The beverage can then be consumed by an animal. In addition to the liquids described herein, the liquid can also be characterized as an aqueous solution. In some embodiments, the aqueous solution is free of alcohol and/or organic solvents. In some embodiments, the solution is free of methanol, isopropanol, ethanol, and/or butanol. In some embodiments a liquid comprising the sugar, cysteine, and/or the sugar-cysteine product is lyophilized to form a powder.

In some embodiments, the pH of the composition (e.g., beverage) is less than or equal to about 7.5. In some embodiments, the pH is from about 4.0 to about 7.5, from about 4.0 to about 7.0, from about 4.0 to about 6.5, from about 4.0 to about 6.0, from about 4.0 to about 5.5, from about 4.0 to about 5.0, from about 4.5 to about 5.0, from about 6.0 to about 7.5, from about 6.0 to about 7.0, from about 6.0 to about 6.5, from about 6.5 to about 7.5, from about 6.8 to about 7.2, from about 6.9 to about 7.1, or from about 7.0 to about 7.5. In some embodiments, the pH is about 7.0. In some embodiments, the pH is from about 2.0 to about 4.0, from about 2.5 to about 4.0, or from about 2.5 to about 3.0. In some embodiments, the pH is about 2.8. In some embodiments, where the pH is less than about 7.5, the pH is such that the composition is safe to ingest.

The present invention also provides aqueous solutions comprising a sugar-cysteine product, wherein the sugar-cysteine product is stable for certain periods of time. Stability of sugar-cysteine product refers to the amount of sugar-cysteine product present in the aqueous solution after a period of time has elapsed when compared to the original amount of sugar-cysteine product present in the solution. For example, if a solution comprises 10% w/v of a sugar-cysteine product and after a period of time the solution still comprises 10% w/v of the sugar-cysteine product, then the solution is 100% stable with respect to the sugar-cysteine product for that particular period of time. Solutions can also be less than 100% stable. For example, after a period of time has elapsed, the solution could still comprise at least 60%, at least 70%, at least 80%, at least 90%, at least 91%, at least 92%, at least 93%, at least 94%, at least 95%, at least 96%, at least 97%, at least 98%, or at least 99% of the original amount of the sugar-cysteine product. Stability can be measured after various periods of time. For example, stability can be measured after 1 day, 1 week, 1 month, 1 year or any fraction thereof. The composition can be stable for at least 1 month, for at least 2 months, for at least 3 months, for at least 4 months, for at least 5 months, or for at least 6 months. In some embodiments, the composition is stable for at least 1 year.

As discussed herein, the composition described herein can be a beverage. The beverage can be placed in various beverage containers. Examples of beverage containers include, but are not limited to, can(s), bottle(s), and pouch(es). Additional examples of beverage containers include those types of containers suitable for dispensing soda, including, for example, kegs. The beverage container can be made of any suitable material such as, but not limited to, glass, plastic, aluminum, or aluminum-coated plastic and the like. In some embodiments, the pouch is a plastic pouch or an aluminum foil pouch. The compositions can also be a powder that can be dissolved in a liquid. The powder can also be contained in a container or a beverage container. The container can be any suitable material such as glass, plastic, or metal (e.g., aluminum). The container can then be opened and the contents can be contacted (e.g., poured) into the liquid. In some embodiments a liquid is added to a container comprising the composition comprising the sugar and the cysteine.

In some embodiments, the beverage or foodstuff comprises at least 10 mg, at least 50 mg, at least 100 mg, at least 200 mg, at least 300 mg, at least 400 mg, at least 500 mg, at least 600 mg, or at least 700 mg of one or more sugar-cysteine products. In some embodiments, the beverage or foodstuff comprises about 10-800 mg, about 10-700 mg, about 10-500 mg, about 10-400 mg, about 10-300 mg, about 10-200 mg, about 10-100 mg, about 10-100, about 50-150, about 75-125, about 50, about 100, about 200, about 300, about 400, or about 500 mg of one or more sugar-cysteine products. The amounts listed herein can be for each sugar-cysteine product. For example, 50 mg of one or more sugar-cysteine products can refer to either one sugar-cysteine product in a composition or the aggregate amount of all the sugar-cysteine products in a composition. In some embodiments, the amounts disclosed herein are calculated per serving. In some embodiments, a serving is 1, 2, 3, 4, 5, 6, 7, 8, 9, 10, 11, or 12 liquid ounces. In some embodiments, the beverage or foodstuff comprises a first, a second, and/or a third sugar-cysteine product. In some embodiments, the sugar-cysteine product is RibCys or GlcCys.

The present invention provides methods of preparing an aqueous solution of a sugar-cysteine product. In some embodiments, the method comprises contacting an aqueous solution with a sugar and cysteine. In some embodiments, the ratio of the sugar to the cysteine is greater than 1.0:1.0. For example, the ratio of sugar to cysteine can be 1.1:1.0, 1.5:1.0, 2.0:1.0, 3.0:1.0, 4.0:1.0, 5.0:1.0, 6.0:1.0, 7.0:1.0, 8.0:1.0, 9.0:1.0, 10.0:1.0, and the like. In some embodiments the ratio of the sugar to cysteine is from about 2.0:1.0 to about 10.0:1.0. In some embodiments, the ratio of the sugar to cysteine is greater than about 2.0:1.0, greater than about 3.0:1.0, greater than about 4.0:1.0, greater than about 5.0:1.0, greater than about 6.0:1.0, greater than about 7.0:1.0, greater than about 8.0:1.0, greater than about 9.0:1.0, or greater than about 10.0:1. In some embodiments the ratio of the sugar to cysteine is from about 2.0:1.0 to about 5.0:1.0.

In some embodiments, the sugar and the cysteine can be contacted with the aqueous solution simultaneously or separately. In some embodiments, the cysteine is contacted with the aqueous solution before the sugar is contacted with the aqueous solution. In some embodiments, the cysteine is contacted with the aqueous solution after the sugar is contacted with the aqueous solution. In some embodiments, the sugar and the cysteine are pre-mixed before contacting the aqueous solution. In some embodiments, the aqueous solution is free of other amino acid(s), mineral(s), vitamin(s), or other compound(s), and the like. The aqueous solution can be filtered or distilled before the sugar or cysteine is added to the solution. In some embodiments, the aqueous solution is water. The water can be, in some embodiments, purified water (e.g., filtered, purified via reverse osmosis, and/or treated with charcoal), distilled water, spring water, or a combination of one or more of these types of water. The water can also be tap water or well water. In some embodiments, the solution is free of glucose, fructose, and/or other ingredients that could be added to water.

In some embodiments, the pH of the aqueous solution is less than or equal to about 7.5. In some embodiments, the pH is from about 4.0 to about 7.5, from about 4.0 to about 7.0, from about 4.0 to about 6.5, from about 4.0 to about 6.0, from about 4.0 to about 5.5, from about 4.0 to about 5.0, from about 4.5 to about 5.0, from about 6.0 to about 7.5, from about 6.0 to about 7.0, from about 6.0 to about 6.5, from about 6.5 to about 7.5, from about 6.8 to about 7.2, from about 6.9 to about 7.1, or from about 7.0 to about 7.5. In some embodiments, the pH is about 7.0. In some embodiments, the pH is from about 2.0 to about 4.0, from about 2.5 to about 4.0, or from about 2.5 to about 3.0. In some embodiments, the pH is about 2.8.

In some embodiments, the temperature of the aqueous solution is greater than 25° C. In some embodiments, the temperature is from about 25° C. to about 95° C. In some embodiments, the temperature of the solution is from about 35° C. to about 95° C., from about 45° C. to about 95° C., from about 55° C. to about 95° C., from about 60° C. to about 95° C., from about 65° C. to about 95° C., from about 75° C. to about 95° C., from about 85° C. to about 95° C., or about 95° C. In those embodiments where the temperature is greater than 25° C., the temperature is less than or equal to the boiling temperature (i.e. boiling point) of the solution.

In some embodiments, the method of making the composition comprises, in the following order: a) contacting the aqueous solution with cysteine to form a cysteine containing aqueous solution; and b) contacting the cysteine containing aqueous solution with the sugar to form an aqueous solution comprising cysteine and sugar. In some embodiments, the method further comprises mixing the solution comprising cysteine and the sugar for a sufficient amount of time such that the cysteine and the sugar form a sugar-cysteine product. In some embodiments, the solution is mixed for about 1 minute to about 120 minutes. The sugar-cysteine product can be any sugar-cysteine product described herein. For example, in some embodiments, the sugar-cysteine product is RibCys and/or GlcCys. In some embodiments, the method comprises preparing RibCys, wherein the solution does not contain glucose, so the solution would also be free of GlcCys.

The method can also comprise a step to monitor the progress of the formation of the sugar-cysteine product. The sugar-cysteine product rate of formation can be monitored, for example, by measuring the amount of free-cysteine in the liquid. As the amount of free-cysteine decreases, this indicates that the reaction is still continuing. In some embodiments, the method can be continued, for example, until there is no free-cysteine left or the amount of free-cysteine has reached a plateau. If there is free-cysteine still remaining in the solution, more sugar (e.g., ribose and/or glucose) can be added such that the free-cysteine is incorporated into the sugar-cysteine product. In some embodiments, the free-cysteine is monitored or quantified using high pressure liquid chromatography (HPLC).

In some embodiments, the method can also comprise contacting one or more additional ingredients with the solution comprising the sugar-cysteine product. In some embodiments, the additional ingredients are mixed together. In some embodiments, the one or more additional ingredients are mixed together at a temperature that is greater than 25° C. In some embodiments, the one or more additional ingredients can be any of the other types of compounds or agents described herein. As discussed herein, in some embodiments, the components of the composition can be added in any order, i.e. the sugar-cysteine does not have to be preformed in the solution before other ingredients are added to the solution. The composition can be made by any method suitable to dissolve the ingredients in the water. The water may be cooled or heated to facilitate the dissolution of the ingredients. For example, in some embodiments, ribose, ribos-cysteine, acetyl-L-carnitine, and vitamin B1 are added to water and dissolved. The solution can then, for example, be heat pasteurized. As discussed herein, the heat pasteurization is an optional step.

In some embodiments, the method comprises mixing the solution until the solution is substantially free of cysteine or free of free-cysteine. In some embodiments, the solution comprises less than 1%, less than 0.5%, or less than 0.1% w/v free-cysteine.

In some embodiments, the cysteine that is added to the aqueous solution is a cysteine salt. In some embodiments, the cysteine salt is the cysteine hydrochloride salt. The method can also comprise contacting the aqueous solution with a sugar, a cysteine salt, and a bicarbonate such as, for example, sodium bicarbonate or potassium bicarbonate.

In some embodiments, the methods further comprise pasteurizing the solution comprising the sugar-cysteine product and/or cold sterilization of the solution comprising the sugar-cysteine product. In some embodiments, the methods comprise filtering the solution comprising the sugar-cysteine product.

The present invention also provides kits for preparing a composition comprising a sugar-cysteine product. In some embodiments, the kit comprises one or more containers comprising a sugar and a cysteine. In some embodiments, the kit comprises a first container comprising a sugar and a second container comprising a cysteine. In some embodiments, the kit comprises a first container comprising a sugar and a cysteine. In some embodiments, the kit comprises a first container comprising a sugar and a cysteine and a second container containing one or more additional ingredients.

In some embodiments, the present invention provides methods of preparing a sugar-cysteine product using the kits described herein. In some embodiments, sugar and cysteine are added to a solution simultaneously. In some embodiments, the sugar and cysteine are pre-mixed before contacting a solution. In some embodiments, the kit comprises instructions for preparing a sugar-cysteine product. In some embodiments, the instructions describe a method described herein. In some embodiments, the kit is for preparing a foodstuff and/or a beverage.

In some embodiments, the present invention provides methods of administering a composition comprising a sugar-cysteine product to an animal. In some embodiments, the method comprises administering or delivering a composition described herein to an animal. In some embodiments, the method comprises an animal drinking a composition described herein. In some embodiments, the method comprises administering or delivering a composition prepared by one or more of the methods described herein to an animal or human.

The present compositions can be employed in methods of use. In some embodiments, the method comprises a method of increasing ATP production in an animal or in a cell comprising administering a composition described herein, including but not limited to, a composition comprising a sugar-cysteine product.

The compositions described herein can also be used to treat or ameliorate the effects of hypoxia. As used herein, the term "hypoxia" or "hypoxic condition" refers to a condition in which oxygen in one or more tissues of an animal (e.g. mammal or human) is lowered below physiologic levels, e.g., to a less than optimal level. Hypoxia can be caused by various stresses including, but not limited to, aerobic exercise, physical weight pressure, anesthesia, surgery, anemia, acute respiratory distress syndrome, chronic illness, chronic fatigue syndrome, trauma, burns, skin ulcers, cachexia due to cancer and other catabolic states and the like.

The compositions described herein can also be used to treat or ameliorate the effects of "ischemia" or "ischemic conditions." Ischemia results when tissues or cells do not receive enough blood. The reduction in blood can be deprive the tissue or cell of sufficient oxygen. Additionally, the energy of the cell or tissue may also be impaired and, therefore, the levels of ATP can drop in a subject suffering from ischemia or an ischemic condition. Accordingly, the compositions described herein can be used in a method of treating ischemia. In some embodiments, the method comprising administering to an animal an amount of a composition comprising a sugar-cysteine product, wherein the product increases ATP in the animal and inhibits the effects of ischemia. Ischemia and/or ischemic conditions can be caused by or result from including, but not limited to, coronary artery disease, cardiomyopathy, including alcoholic cardiomyopathy, angioplasty, stenting, heart surgery such as bypass surgery or heart repair surgery ("open-heart surgery"), organ transplantation, prolonged weight pressure on tissues (pressure ulcers or bedsores), ischemia-reperfusion injury which can cause damage to transplanted organs or tissue, and the like.

The present compositions can be used to increase glutathione in an animal. In some embodiments, the method comprises administering to the animal an effective amount of a composition described herein, wherein the amount increases the amount of glutathione and/or ATP in the animal. In some embodiments, the animal is suffering from hypoxia or ischemia.

Effective amounts of a composition described herein will vary dependent upon the condition, age and weight of the animal administered the composition, the condition to be treated and the mode of administration. Both cysteine, as released in vivo from a sugar-cysteine product (e.g. ribose-cysteine) in animal models, and ribose, as administered directly to humans, have been found to be essentially non-toxic over wide dosage ranges. For example, ribose has been reported to increase exercise capacity in healthy humans when taken orally at dosages of 8-10 g per day by an adult. See U.S. Pat. No. 6,534,480. RibCys administered to mice at 8 mmol/kg i.p., increased glutathione levels in numerous organs, including heart (1.5.times.) and muscle tissue (2.5.times.). See, J. C. Roberts, Toxicol. Lett., 59, 245 (1991) Likewise, RibCys at 8 mmol/kg has been found to deliver effective protective amounts of cysteine to mice exposed to cyclophosphamide. This dose can deliver about 70-80 g of ribose and about 60-70 g of cysteine to an adult human. See J. C. Roberts, Anticancer Res., 14, 383 (1994). Doses of 2 g/kg RibCys were reported to protect mice against acetaminophen hepatic and renal toxicity by A. M. Lucas et al., Toxicol. Pathol., 20, 697 (2000). Doses of 1 g/kg RibCys were reported to protect mice against irradiation-induced bowel injury (see J. K. Rowe et al., Dis. Colon Rectum, 36, 681 (1993). J. E. Fuher (U.S. Pat. No. 4,719,201) reported that doses of ribose of about 3 g/day for at least 5 days effectively restored and maintained ATP levels in dogs subjected to ischemia (heart attack model), doses that delivered about 550-700 mg/kg of ribose to an 30 kg dog.

The compositions described herein can be administered in any form including, but not limited to, a pharmaceutical unit dosage form comprising the active ingredient in combination with a pharmaceutically acceptable carrier, which can be a solid, semi-solid, or liquid diluent. A unit dosage of the compound can also be administered without a carrier material. Examples of pharmaceutical preparations include, but are not limited to, tablets, powders, capsules, aqueous solutions, suspensions including concentrates, liposomes, and other slow-releasing formulations, as well as transdermal delivery forms. Typically, the unit dosage form includes about 0.001-99% of the active substance.

The compositions can be delivered by any suitable means, e.g., topically, orally, parenterally. In some embodiments, the delivery form is liquid or a solid such as a powder that can be stirred into an ingestible liquid. Standard pharmaceutical carriers for topical, oral, or parenteral compositions may be used, many of which are described in Remington's Pharmaceutical Sciences, Mack Publishing Co., Easton, Pa.

For example, for oral administration, suitable pharmaceutical carriers or diluents can include mannitol, lactose, starch, magnesium stearate, talcum, glucose, and magnesium carbonate. Oral compositions can be in the form of tablets, capsules, powders, solutions, suspensions, sustained release formulations, and the like. A typical tablet or capsule can contain 40-99% lactose, 1-2% magnesium stearate, and 10-20% cornstarch, along with the active substance (e.g. about 0.001-20%). As discussed herein an aqueous solution can contain up to the saturation level of a sugar-cysteine product or its salt. In some embodiments, the aqueous solution comprises an amount of the sugar that is effective to prevent or inhibit premature in vitro dissociation.

For parenteral administration, suitable pharmaceutical carriers can include water, saline, dextrose, Hank's solution, Ringer's solution, glycerol, and the like. Parenteral compositions can be in the form of suspensions, solutions, emulsions, and the like. Parenteral administration is usually by injection or infusion which can be subcutaneous, intramuscular, or intravenous. Other uses and methods for administering a sugar-cysteine product can be found, for example, in U.S. Publication No. 20090042822, which is hereby incorporated by reference in its entirety.

The present invention is now described with reference to the following example. The example is provided for the purpose of illustration only and the invention should in no way be construed as being limited to the example, but rather should be construed to encompass any and all variations which become evident as a result of the teaching provided herein. Those of skill in the art will readily recognize a variety of non-critical parameters that could be changed or modified.

EXAMPLE 1

Preparation of Beverage (Prophetic)

A beverage comprising RibCys is prepared by mixing D-ribose and L-cysteine with water, wherein the ratio of D-ribose to L-cysteine is 2:1. The ribose and cysteine are mixed at room temperature until the cysteine is completely dissolved.

What is claimed is:

1. A composition comprising RibCys, ribose, acetyl-L-carnitine, vitamin B1, vitamin B2, vitamin B3, vitamin B6, vitamin B12, folic acid, panthothenic acid, biotin, chromium, magnesium, copper, quercetin, CoQ10, ginseng, and rhodiola rosea and caffeine.

2. A beverage container comprising the composition of claim 1.

3. A beverage comprising the composition of claim 2.

4. The composition of claim 2, wherein the composition consists essentially of RibCys, ribose, acetyl-L-carnitine, vitamin B1, vitamin B2, vitamin B3, vitamin B6, vitamin B12, folic acid, panthothenic acid, biotin, chromium, magnesium, copper, quercetin, CoQ10, ginseng, and rhodiola rosea and caffeine.

5. The composition of claim 2, wherein the composition consists of RibCys, ribose, acetyl-L-carnitine, vitamin B1, vitamin B2, vitamin B3, vitamin B6, vitamin B12, folic acid, panthothenic acid, biotin, chromium, magnesium, copper, quercetin, CoQ10, ginseng, and rhodiola rosea and caffeine.

* * * * *